United States Patent
Holthuizen et al.

(10) Patent No.: US 12,251,172 B2
(45) Date of Patent: Mar. 18, 2025

(54) NAVIGATION SUPPORT

(71) Applicant: KONINKLIJKE PHILIPS N.V., Eindhoven (NL)

(72) Inventors: Ronaldus Frederik Johannes Holthuizen, Culemborg (NL); Robert Johannes Frederik Homan, Batenburg (NL); Jarich Willem Spliethoff, Utrecht (NL); Bernardus Hendrikus Wilhelmus Hendriks, Eindhoven (NL); Peter George Van De Haar, Eindhoven (NL); Johanneke Gerrigje Groen, Veldhoven (NL); Jan Rongen, Eindhoven (NL); Edward Vuurberg, Eindhoven (NL); Johan Juliana Dries, Arendonk (BE); Christian Reich, Eindhoven (NL); Keshav Simhadri, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 126 days.

(21) Appl. No.: 18/270,533

(22) PCT Filed: Dec. 28, 2021

(86) PCT No.: PCT/EP2021/087696
§ 371 (c)(1),
(2) Date: Jun. 30, 2023

(87) PCT Pub. No.: WO2022/148688
PCT Pub. Date: Jul. 14, 2022

(65) Prior Publication Data
US 2024/0065773 A1 Feb. 29, 2024

(30) Foreign Application Priority Data
Jan. 8, 2021 (EP) .................................... 21150736

(51) Int. Cl.
A61B 34/00 (2016.01)
A61B 34/20 (2016.01)
A61B 90/00 (2016.01)

(52) U.S. Cl.
CPC ............ *A61B 34/20* (2016.02); *A61B 90/361* (2016.02); *A61B 90/39* (2016.02); *A61B 2034/2051* (2016.02); *A61B 2090/376* (2016.02)

(58) Field of Classification Search
CPC ....................................................... A61B 34/20
See application file for complete search history.

(56) References Cited

U.S. PATENT DOCUMENTS 6,978,167 B2 12/2005 Dekel et al.
8,553,839 B2 10/2013 Hendriks et al.
(Continued)

FOREIGN PATENT DOCUMENTS

DE 102010018291 A1 10/2011
WO 2017042171 A1 3/2017
(Continued)

OTHER PUBLICATIONS

Peh et al., "Accuracy of augmented reality surgical navigation for minimally invasive pedicle screw insertion in the thoracic and lumbar spine with a new tracking device", The Spine Journal, 20, (2020), pp. 629-637.
Fassi et al., "An image based method to synchronize cone-beam CT and optical surface tracking", Journal of Applied Clinical Medical Physics, vol. 16, No. 2, (2015), pp. 117-128.
Stryker Navigation Brochure, Spine Navigation System, downloaded Jun. 29, 2023.
Medtronic, Stealthstation S7 floor system brochure, www.medtronicneurosurgery.com, downloaded on Jun. 29, 2023.
(Continued)

Primary Examiner — Joseph M Santos Rodriguez

(57) ABSTRACT

The present invention relates to guidance during a medical intervention. In order to provide an improved navigation support with a facilitated setup, a system (10) for navigation support is provided. An image data input (12) receives a plurality of acquired 2D X-ray images of a subject's body from different angles. A set of markers, which are visible in
(Continued)

X-ray images and which are detectable by a navigation system, is assigned to the subject. A marker detecting arrangement (16) is provided that detects a current spatial location of the markers assigned to the subject. A data processor (14) reconstructs a 3D volume of the subject based on the plurality of 2D X-ray images. At least a part of the markers is arranged outside the volume covered by the reconstructed 3D volume of the subject, while the markers are visible in the 2D X-ray images. The data processor (14) identifies the markers in the 2D X-ray images based on image data of the plurality of 2D X-ray images outside the 3D volume and determines a spatial location of the markers in relation to the 3D volume of the subject. The data processor (14) also registers the reconstructed 3D volume of the subject to a current spatial position of the subject based on the detected current spatial location of the markers and the determined spatial location of the markers in relation to the 3D volume of the subject. An output interface (18) provides the registered reconstructed 3D volume for navigation.

13 Claims, 6 Drawing Sheets

(56) References Cited

U.S. PATENT DOCUMENTS

| 9,005,211 B2 | 4/2015 | Brundobler et al. |
| 9,254,106 B2 | 2/2016 | Berlinger et al. |
| 9,610,056 B2 | 4/2017 | Lavallee et al. |
| 2019/0328466 A1 | 10/2019 | Schwägli |

FOREIGN PATENT DOCUMENTS

| WO | 2017103046 A2 | 6/2017 |
| WO | 2018056563 A1 | 3/2018 |

OTHER PUBLICATIONS

Medtronic, Stealthstation® S7® Integrated Navigation System, (2013), www.medtronicneurosurgery.com.
Medtronic Fusion ENT Navigation System, 2009, Medtronic, Inc., www.MedtronicENT.com.
Spine Navigation Brochure, brianlab.com, 2013 Brianlab AG, pp. 1-19.
BrainLab Intuitive Navigation and Planning, © 2010 Brainlab AG. Printed in Germany. ENT-FL-E-ENT 0308 Rev.2 Q:5,000 ®registered trademark of Brainlab AG in Germany and/or the US ™trademark of Brainlab AG in Germany and/or the US.
International Search report and Written Opinion of PCT/EP2021/087696, dated Mar. 25, 2022.

NAVIGATION SUPPORT

CROSS-REFERENCE TO PRIOR APPLICATIONS

This application is the U.S. National Phase application under 35 U.S.C. § 371 of International Application No. PCT/EP2021/087696, filed on Dec. 28, 2021, which claims the benefit of European Patent Application Serial No. 21150736.3, filed on Jan. 8, 2021. These applications are hereby incorporated by reference herein.

FIELD OF THE INVENTION

The present invention relates to guidance during a medical intervention, and relates in particular to a system for navigation support, to a navigated X-ray imaging arrangement for medical interventions of a subject and to a method for navigation support.

BACKGROUND OF THE INVENTION

Increasingly more surgical procedures are performed minimally invasive. Various solutions have been developed the last couple of years to improve the ease of use and the obtainable accuracy for the surgeons. In some examples, patient and device tracking is combined with registration of e.g. pre-operative CT or MRI images. As an example, U.S. Pat. No. 8,553,839 B2 provides a system for generating an image including information of both an interior and an exterior of a patient. The system includes an X-ray device for providing an X-ray image of a patient's interior, and a camera responsive to a wavelength for providing a camera image of a patient's exterior. The camera may be supported by the X-ray device for establishing a determined spatial relationship between the camera and the X-ray device. The system further includes a spatial reference for spatially correlating the X-ray image and the camera image, where the spatial reference is detectable in the X-ray image and in the camera image. A data processor is configured for rendering the camera image and the X-ray image into a composite image on the basis of the spatial reference. An example for registration of 3D CT image data, e.g. cone beam CT acquisitions in navigation systems, is image based analysis, e.g. segmentation, of X-ray visible markers with a known association to optical markers in the 3D imaging volume. However, it has been shown that in imaging systems with a relatively small field of view, such as mobile 3D capable C-arm systems, it might not be possible to capture both the anatomy of interest and the X-ray visible markers at the same time.

SUMMARY OF THE INVENTION

There may thus be a need to provide an improved navigation support with a facilitated setup.

The object of the present invention is solved by the subject-matter of the independent claims; further embodiments are incorporated in the dependent claims. It should be noted that the following described aspects of the invention apply also for the system for navigation support, for the navigated X-ray imaging arrangement for medical interventions and for the method for navigation support.

According to the present invention, a system for navigation support is provided. The system comprises an image data input, a data processor, a marker detecting arrangement and an output interface. The marker detecting arrangement is configured to detect a current spatial location of markers assigned to the subject. The image data input is configured to receive a plurality of acquired 2D X-ray images of a subject's body from different angles. A set of markers, which are visible in X-ray images and which are detectable by a navigation system, is assigned to the subject. The data processor is configured to reconstruct a 3D volume of the subject based on the plurality of 2D X-ray images. At least a part of the markers is arranged outside the volume covered by the reconstructed 3D volume of the subject, while the markers are visible in the 2D X-ray images. The data processor is also configured to identify the markers in the 2D X-ray images based on image data of the plurality of 2D X-ray images outside the 3D volume and determine a spatial location of the markers in relation to the 3D volume of the subject. The data processor is further configured to register the reconstructed 3D volume of the subject to a current spatial position of the subject based on the current spatial location of the markers as detected by the marker detecting arrangement and the determined spatial location of the markers in relation to the 3D volume of the subject. The output interface is configured to provide the registered reconstructed 3D volume for navigation support.

As an advantageous effect, the markers do not need to be arranged within the region of interest as defined by the reconstructed 3D volume as 3D field of view, but can be assigned outside the narrow 3D field of view, while still inside the wider 2D field of view. Thus, for example, in case of open surgery, a further distanced arrangement of the markers can be used providing more working space for the surgeon regarding the operation field. As another example, for minimally invasive spine surgery, the markers can be located on or above the skin, while the X-ray imaging and in particular the 3D volume reconstruction can be focused on the spine, excluding the skin area or above.

According to a first example, for the determination of the spatial location of the markers in relation to the 3D volume of the subject, the data processor is configured to use 2D image data from the 2D X-ray images outside the 3D volume and to detect the markers in said 2D image data.

According to a second example, for the determining of the spatial location of the markers in relation to the 3D volume of the subject, the data processor is configured to provide an extended field of view reconstruction visualizing high-contrast items (such as the markers) or items with a-priori knowledge regarding its shape or X-ray absorption properties outside the reconstructed 3D volume of the subject.

According to an example, the marker detecting arrangement comprises a plurality of optical trackers, e.g. optical cameras configured to detect the markers. These cameras may for example be provided attached to a mobile base structure, to a ceiling support and/or, in certain embodiments, integrated in the housing of an X-ray detector of a C-arm X-ray system Alternatively or in addition, non-optical navigation systems can be provided. In another example, a plurality of electromagnetic trackers, e.g. electromagnetic sensors is provided attached to a mobile base structure, the electromagnetic sensors being configured to detect the markers. In a further example, a plurality of ultrasound-based trackers, e.g. ultrasound-based trackers is provided attached to a mobile base structure, the electromagnetic sensors being configured to detect the markers.

According to an example, for the detection of the markers in the 2D image data from the 2D X-ray images outside the 3D volume, or in the extended field of view reconstruction, at least one of the group of information about the shape and X-ray absorption properties of the markers is provided and used for artifact correction before detection of the markers.

According to the present invention, also a navigated X-ray imaging arrangement for medical interventions of a subject is provided. The arrangement comprises a system for navigation support according to one of the preceding examples. The arrangement also comprises an X-ray imaging system, e.g. a mobile system or a non-mobile system. The X-ray imaging system is configured to acquire 2D X-ray images from a plurality of angles for providing the plurality of acquired 2D X-ray images of a subject's body. The navigation arrangement is configured to link a spatial coordinate system of the X-ray imaging system with a spatial coordinate system of the system for navigation support.

According to an example, a plurality of at least two markers is provided, which markers are configured for temporal assignment to the subject. For instance, the markers may be assigned to the subject outside a region of interest, which region of interest is set to be covered by the reconstructed 3D volume.

According to an aspect, also a method for navigation support is provided. The method comprises the following steps:
  acquiring a plurality of 2D X-ray images of a subject's body from different angles; wherein a set of markers, which are visible in X-ray images and which are detectable by a navigation system, is assigned to the subject;
  reconstructing a 3D volume of the subject based on the plurality of 2D X-ray images; wherein at least a part of the markers is arranged outside the volume covered by the reconstructed 3D volume of the subject, while the markers are visible in the 2D X-ray images;
  identifying the markers in the 2D X-ray images based on image data of the plurality of 2D X-ray images outside the 3D volume and determining a spatial location of the markers in relation to the 3D volume of the subject;
  detecting a current spatial location of the markers assigned to the subject;
  registering the reconstructed 3D volume of the subject to a current spatial position of the subject based on the detected current spatial location of the markers and the determined spatial location of the markers in relation to the 3D volume of the subject; and
  providing the registered reconstructed 3D volume for navigation support.

According to an aspect, a navigated X-ray imaging system is provided that comprises an X-ray imaging system, capable of reconstructing 3D X-ray images of the subject's interior by combining information from a set of 2D X-ray images that have different angulation with respect to the subject, i.e. the subject's body.

Further, a navigation system is provided that comprises optical cameras or electromagnetic tracking capable of tracking markers assigned to a subject's body. In another example, an ultrasound based navigation system is provided.

Navigation systems may comprise different types of tracking. For example, optical tracking is provided with cameras. In another option, optical tracking is provided with, for example, optical sensors and optical transmitters for beam generation. For another example, ultrasound tracking is provided based on the principle of echolocation. For a further example, radiofrequency-based tracking is provided. Other combinations and fusions are also provided.

As a further example, single-camera optical tracking is provided.

Still further, markers are provided that can be detected both by the X-ray imaging system and the navigation system.

Furthermore, a processor is provided that is capable of receiving the data from the X-ray imaging system and calculating the 3D position of the markers. In particular, a subset of the 2D X-ray images is used to calculate the 3D position of the markers in the 3D X-ray imaging coordinate system and link this to the 3D coordinate system of the navigation system.

In an example, the navigation system is provided as a mobile satellite with a plurality of cameras, e.g. four cameras. The navigation system is attached to the mobile view station trolley by a mechanical support arm. The X-ray system is a mobile C-arm capable of 3D imaging. Markers that are visible on X-ray and by the navigation cameras are attached to the subject. The position of the markers is within the 3D cone beam CT volume, but not used for the 3D image data generation. The position of the markers is calculated and transferred to the navigation system. Because the markers are visible both the in 3D cone beam CT volume and optically by the camera system, the registration process of matching the X-ray 3D data to the optical navigation system can be completed.

In a further example, an image data input receives a plurality of acquired 2D X-ray images of a subject's body from different angles. A set of markers, which are visible in X-ray images and which are detectable by a navigation system, is assigned to the subject. A marker detecting arrangement is provided that detects a current spatial location of the markers assigned to the subject. A data processor reconstructs a 3D volume of the subject based on the plurality of 2D X-ray images. At least a part of the markers is arranged outside the volume covered by the reconstructed 3D volume of the subject, while the markers are visible in the 2D X-ray images. The data processor identifies the markers in the 2D X-ray images based on image data of the plurality of 2D X-ray images outside the 3D volume and determines a spatial location of the markers in relation to the 3D volume of the subject. The data processor also registers the reconstructed 3D volume of the subject to a current spatial position of the subject based on the detected current spatial location of the markers and the determined spatial location of the markers in relation to the 3D volume of the subject. An output interface provides the registered reconstructed 3D volume for navigation.

In an example, both options are provided in combination: Detecting the markers in said 2D image data outside the image parts used for 3D reconstruction and providing an extended field of view for marker location determination.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
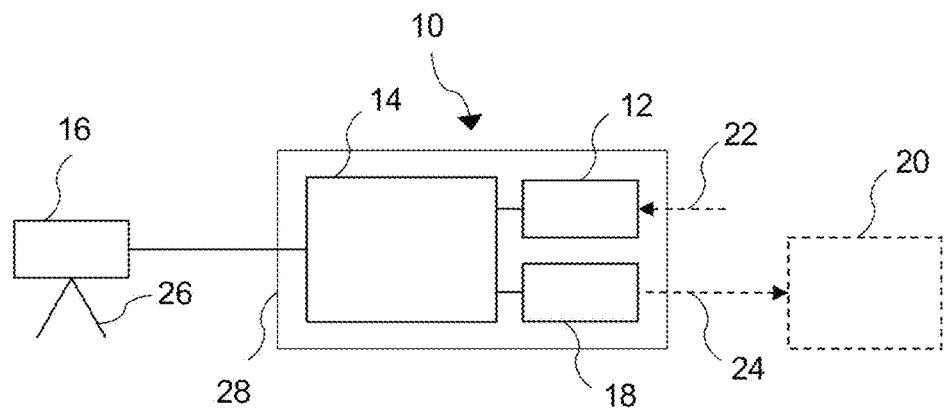
FIG. 1 schematically shows an example of a system for navigation support.

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well-known functions or constructions are not described in detail since they would obscure the embodiments with unnecessary detail. Moreover, expressions such as "at least one of", when preceding a list of elements, modify the entire list of elements and do not modify the individual elements of the list.

FIG. 1 schematically shows an example of a system 10 for navigation support. The system 10 comprises an image data input 12, a data processor 14, a marker detecting arrangement 16 and an output interface 18. The marker detecting arrangement 16 is configured to detect a current spatial location of markers assigned to the subject. The image data input 12 is configured to receive a plurality of acquired 2D X-ray images of a subject's body from different angles. A set of markers, which are visible in X-ray images and which are detectable by a navigation system, is assigned to the subject (see also FIG. 2 and FIG. 5). The data processor 14 is configured to reconstruct a 3D volume of the subject based on the plurality of 2D X-ray images. At least a part of the markers is arranged outside the volume covered by the reconstructed 3D volume of the subject, while the markers are visible in the 2D X-ray images. The data processor 14 is also configured to identify the markers in the 2D X-ray images based on image data of the plurality of 2D X-ray images outside the 3D volume and to determine a spatial location of the markers in relation to the 3D volume of the subject. The data processor 14 is further configured to register the reconstructed 3D volume of the subject to a current spatial position of the subject based on the detected current spatial location of the markers and the determined spatial location of the markers in relation to the 3D volume of the subject. The output interface 18 is configured to provide the registered reconstructed 3D volume for navigation.

The term "assigned" refers to identifiable objects that may be provided in an at least temporarily fixed arrangement with the subject.

In a first option, the markers are provided as separate markers that are attached to the subjects, e.g. on the skin of a subject.

In a second option, the markers are provided as anatomical markers, i.e. physical properties of a subject that are visible in both X-ray and optical tracking.

In a further option, the markers are provided as implants of a subject that are visible in both X-ray and electromagnetic tracking.

Figure 2:
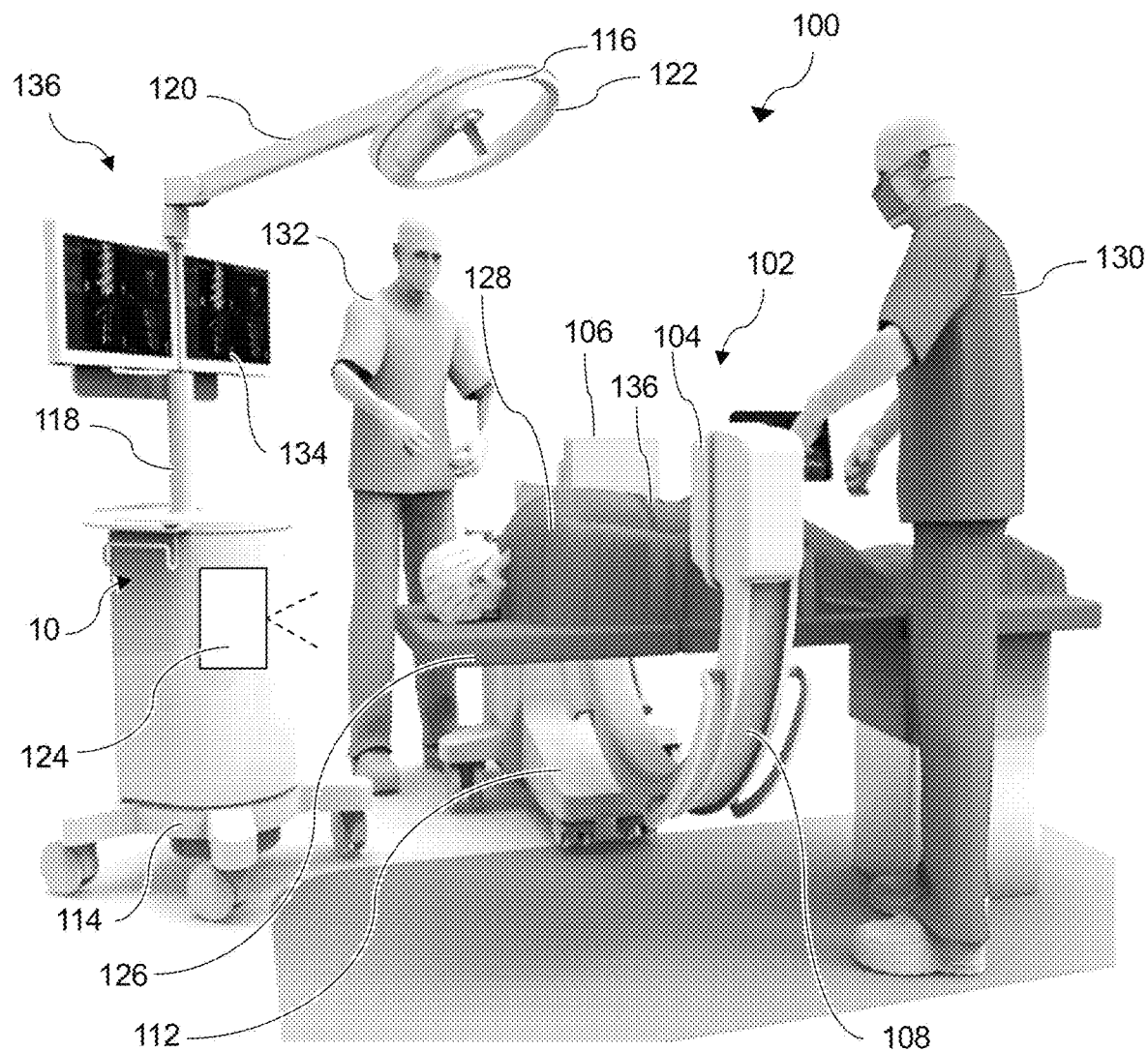
FIG. 2 shows a navigated X-ray imaging arrangement for medical interventions of a subject.

A dotted frame 20 indicates the further use of the registered reconstructed 3D volume, for example in a navigation system or another system like the navigated X-ray imaging arrangement shown in FIG. 2.

Further, a first arrow 22 indicates receiving the plurality of acquired 2D X-ray images by the image data input 12. A second arrow 24 indicates providing the registered reconstructed 3D volume for navigation by the output interface 18. The detection of a current spatial location of the markers is indicated by two lines of an indicated detecting angle 26.

A frame 28 indicates an option to provide the image data input 12, the data processor 14 and the output interface 18 in a common structure, e.g. a common housing. The marker detecting arrangement 16 is separate in the example shown, but another example is provided, where the marker detecting arrangement 16 is also provided in an integrated manner. As a further option, the image data input 12, the data processor 14 and the output interface 18 are arranged as separate components data-connected with each other.

The system 10 for navigation support can also be referred to as navigation support system or system for navigation.

It is noted that in an option, the system 10 for navigation support is specific to an imaging system, i.e. implemented within the context of the imaging system with the output of the system for navigation support being used by a navigation system.

In another option, the system 10 for navigation support is specific to a navigation system, i.e. implemented within the context of the navigation system with the output of the system for navigation support being used by the navigation system.

Thus, it is provided to perform marker segmentation on image parts of 2D X-ray images that are provided for a 3D reconstruction, but the markers visible in these image parts are not part of the produced reconstruction volume (because insufficient 2D x-ray image projections were acquired where the marker is visible). In an option, the 3D location of these markers is calculated. In another option, a use of extended field of view reconstruction is provided.

As an advantage, different types of image acquisition systems can be used, since there is no need for placing optical markers on the system. Imaging system and navigation system can be provided independent from each other. This provides improved compatibility.

As a further advantage, manually performing a registration is avoided, e.g. by using an optically tracked pointer and indicating several points on the patient, which manual registration can be prone to error and is time consuming.

A still further advantage is that registration is possible even when the location of the anatomy of interest is further away from the possible location of the X-ray visible markers.

Briefly said, the system 10 for navigation support provides that automatic registration between X-ray imaging systems and optical navigation system based on X-ray visible markers even works with a smaller field of view X-ray system.

The image data input 12 is configured to receive the plurality of acquired 2D X-ray images of the subject's body from an X-ray imaging system.

Figure 5A:
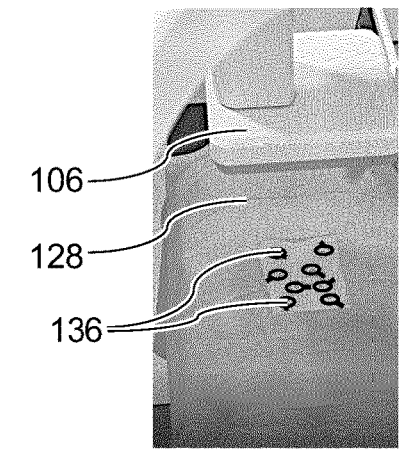
FIG. 5a shows another example of the markers of FIG. 5.
Figure 5:
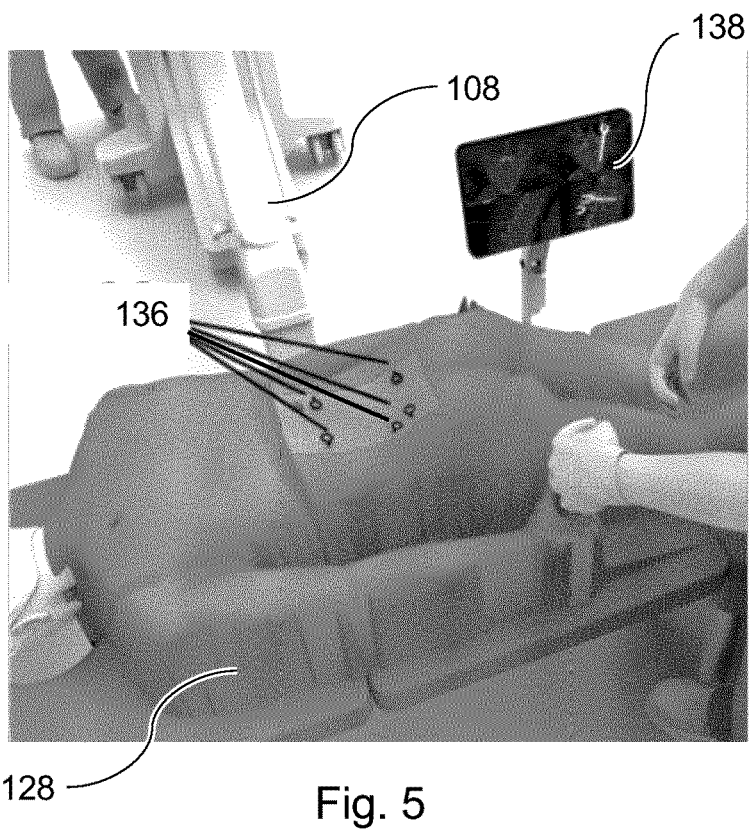
FIG. 5 shows an example of a set of markers temporarily assigned to a subject.

In an example, the system 10 for navigation support comprises a plurality of at least two markers for assignment to the subject (see also FIG. 5).

As an effect, the system 10 for navigation support is provided that allows to link the coordinate system, also referred to as spatial reference or spatial grid, of the navigation system with the respective coordinate system of any X-ray imaging system that provides the 2D X-ray images of the subject. The registration, i.e. link of the two coordinate systems provides and allows a transfer from the X-ray imaging space into the optical navigation space and vice versa.

In an alternative option, if the geometric pattern of multiple X-ray visible markers is known a-priori, a single image is provided for registration, instead of plurality of acquired 2D X-ray images.

In an option, the registration of the reconstructed 3D volume of the subject is provided by an imaging system, and the result provided to the system 10 for navigation support.

In a further option, the registration of the reconstructed 3D volume of the subject is provided by a navigation system, and the result provided to the system 10 for navigation support.

In an example (not further shown in FIG. 1), the registration is achieved by some navigation system dependent measurement systems, like 3D optical tracking, electromagnetic (EM) tracking and the like. In another example, the navigation system is ultrasound based.

In an option, the system 10 for navigation support is provided as a support system in the context of an arrangement provided for navigation or imaging or both.

In a first option, the system 10 for navigation support is provided as a navigation system, or as a part of such system, configured for providing navigation during medical interventions or medical examinations. The navigation system may thus be a support system in a cathlab.

In a second option, the system 10 for navigation support is provided as an imaging system, or as a part of such system, configured for providing imaging during medical interventions or medical examinations. The imaging system may thus be a support system in a cathlab.

In a third option, the system 10 for navigation support is provided as a navigation-imaging system (or imaging-navigation system), or as a part of such system, configured for providing navigation and imaging during medical interventions or medical examinations. The imaging-navigation system may thus be a support system in a cathlab. FIG. 2 shows an example of a navigated X-ray imaging arrangement 100 for medical interventions of a subject. The arrangement 100 comprises the system 10 for navigation support according to one of the preceding examples. The arrangement 100 also comprises an X-ray imaging system 102. The X-ray imaging system 102 is configured to acquire 2D X-ray images from a plurality of angles for providing the plurality of acquired 2D X-ray images of a subject's body. The arrangement is configured to link a spatial coordinate system of the X-ray imaging system 102 with a spatial coordinate system of the system 10 for navigation support.

The data processor 14 of the system 10 for navigation support links the two spatial coordinate systems.

The X-ray imaging system 102 comprises an X-ray source 104 and an X-ray detector 106, for example attached to ends of a movable C-arm structure 108. In an option of the navigated X-ray imaging arrangement 100, the X-ray imaging system 102 is a mobile X-ray imaging system, such as a mobile C-arm system having the C-arm structure 108 attached to a mobile imaging base 112. In an alternative option, also a non-mobile imaging system is provided, for example a C-arm system that is permanently installed in a catheterization lab (cathlab) or hybrid operating room, mounted either to the ceiling or the floor of the room. The navigated X-ray imaging arrangement 100 can also be referred to as navigated X-ray imaging system.

As an option of the system 10 for navigation support according to FIG. 1, a mobile base structure 114 is shown, e.g. as a part of a navigation system. The marker detecting arrangement comprises a plurality of optical cameras 116, which in this example is attached to the mobile base structure 114. The cameras 116 are configured to detect the markers. For example, a vertical post 118 with a movable upper arm 120 is provided, to which a ring-like support 122 for the optical cameras 116 is provided (see also FIG. 4).

In an alternative embodiment (not shown), for a ceiling-mounted fixed C-arm system, the marker detecting arrangement with the cameras 116 may also be mounted to the ceiling of the room by means of a dedicated boom or arm. It is also possible to integrate some or all of the cameras 116 into the housing of the X-ray detector 106 of the fixed C-arm system in this embodiment.

In further options (not shown), the optical cameras are attached to a fixed base structure or to a fixed wall-mounted support structure, for example.

In an example, indicated in FIG. 2 as an option, an electromagnetic tracking arrangement 124 with a number of electromagnetic trackers (not shown) is provided attached to a base, e.g. to the mobile base structure 112. The electromagnetic tracking arrangement 124 is configured to detect the markers.

In a further option, not shown, the electromagnetic tracking arrangement is attached to a fixed structure, e.g. to a fixed base structure, to a fixed wall-mounted support structure or to a fixed ceiling-mounted support structure. As an example, electromagnetic trackers are attached to the object support, also referred to as patient table.

In an example, for the detection of the markers in the 2D image data from the 2D X-ray images outside the 3D volume, or in the extended field of view reconstruction, at least one of the group of information about the shape of the markers and X-ray absorption properties of the markers is provided and used for artifact correction before detection of the markers.

As an example, high-contrast items such as the markers are thus visualized to an extent that is sufficient for marker location determination.

In a first example, for the determination of the spatial location of the markers in relation to the 3D volume of the subject, the data processor 14 is configured to use 2D image data from the 2D X-ray images outside the 3D volume and to detect the markers in said 2D image data.

The markers are present in a too small subset of 2D images that would cause artifacts in the 3D reconstruction if the field of view of the 3D reconstruction would be big enough to encompass the spatial location of the markers. The image portions used for the 3D volume reconstruction are thus marker-free or marker-less. Simply said, the markers are insufficiently present in the images that are used for 3D volume reconstruction.

In a first option of a model based solution, X-ray visible markers are detected on a subset of the 2D X-ray images used to perform the 3D cone beam CT/XperCT reconstruction. A specific shape or pattern of the X-ray visible markers (such as knowledge that a set of round spheres has been employed) is used to enable accurate 3D position determination of these markers in relationship of the 3D cone beam CT/XperCT reconstruction volume.

As an example, detection of 3D objects is provided by performing a reconstruction with a limited set of 2D X-ray images. The simplest form is detection of round spheres with a known diameter, of which an accurate 3D position can be reconstructed based on just two 2D X-ray images from different angulations. More advanced shapes can also be reconstructed if a-priori shape information is known. For specific marker arrangements, the 3D positions can be calculated using a single 2D X-ray image, although the usage of multiple images is preferred to minimize the depth error of said calculation.

Knowledge of the position of these markers and the 3D CBCT volume information is transferred to the optical navigation system.

Knowledge of the position of markers can also be electromagnetic based (EM-based), ultrasound based (US-based) or by other technology navigation systems.

As an example, the position of the markers can be transferred explicitly for example via DICOM metadata, or they can be encoded in the 3D reconstructed volume. Example of the latter is by increasing the volume size of the reconstruction and by performing a 3D reconstruction of the X-ray markers in the "extended field of views" area, while only performing anatomical reconstruction on the original field of view subset of the 3D volume. Another example is the placement of synthetic markers at the calculated marker positions.

The optical navigation system performs automatic registration of the 3D cone beam CT volume to the optical navigation space using the X-ray marker positions. As an example, the position of the X-ray visible markers is used or detected in the extended field of view area, similar as with large field of view automatic registration methods.

In an example, it is provided a known correlation of (optical) markers visible by the navigation system and X-ray markers visible by the imaging system. As an option, markers are provided that are visible in both systems, but an arrangement of optical markers and X-ray markers in a known pattern is also provided as another option.

In a second example, for the determining of the spatial location of the markers in relation to the 3D volume of the subject, the data processor 14 is configured to provide an extended field of view reconstruction visualizing high-contrast items (such as the markers) or items with a-priori knowledge regarding its shape or X-ray absorption properties outside the reconstructed 3D volume of the subject.

The markers are not or insufficiently present in the reconstructed 3D volume. The reconstructed 3D volume is thus marker-free or marker-less.

In a further option of an extended field of view based solution, extended field of view reconstruction is used to enable visualization of high-contrast items or items with a-priori knowledge regarding its shape or X-ray absorption properties outside the standard field of view FOV of the cone beam CT (CBCT) volume. That is, the standard FOV of the CBCT volume corresponds to a "core" of the extended 3D volume, for which core 3D image data of the anatomy of the subject can be calculated.

The reconstruction in the "extended" field of view beyond the core is not used for generating 3D image data to avoid causing image artifacts of the anatomy, which may result in a risk is of misinterpretation or wrong guidance during the navigation procedure, resulting in patient harm, specifically for the spatial locations that can be expected to suffer for these artifacts. For this extended FOV, only 3D markers are reconstructed from (sparse) 2D image data in which such high-contrast items and/or items matching a specific (projected) marker shape or X-ray absorption characteristics appear.

To avoid, for example, patient harm during navigation, it is proposed to make all voxels outside the standard field of view black that are below a certain threshold and/or draw a ring in the XperCT volume indicating the artifact-free field of view area of the scan. Image distortions will also affect the shape of the X-ray visible markers used for registration, but if simple shapes (such as spheres) are used, the center of gravity of the sphere (or ellipsoid-like reconstructed structure) will be preserved in some cases, as also explained in the context of FIGS. 9a-9b.

Optionally, a dedicated filter or post-processing step can be used to correct for the predictable artifacts. For example, if the shape of the marker is known, e.g. a 5 mm round sphere, the artifact can be predicted and corrected. This correction includes the geometric representation of the marker as well as the image (Hounsfield) intensity of the marker in the 3D volume. Also the intensity drop can be corrected. Such a correction would avoid modification of the marker detection algorithm on the navigation system or resolves inaccuracies of existing marker detection and registration algorithms of the navigation system, as the appearance of the marker will be similar as if the marker was inside the regular field of view of the reconstruction. The further the distance of the X-ray visible marker to the standard field of view, the greater the need to know a-priori information of the marker to compensate for artifacts.

FIG. 2 also shows a subject support 126 to arrange a subject 128 between the X-ray source 104 and the X-ray detector 106 for X-ray imaging. FIG. 2 shows an exemplary situation with a first staff member 130 and a second staff member 132 arranged next to the subject support 126.

A display arrangement 134 is provided, e.g. for operating the system 10 for navigation support or the navigated X-ray imaging arrangement 100.

In an example, the mobile base structure 114, the vertical post 118 with the movable upper arm 120 and the ring-like support 122 with the attached optical cameras 116 provide basic parts of a mobile navigation system 136. In an option, the mobile navigation system 136 also comprises the display arrangement 134.

Figure 3:
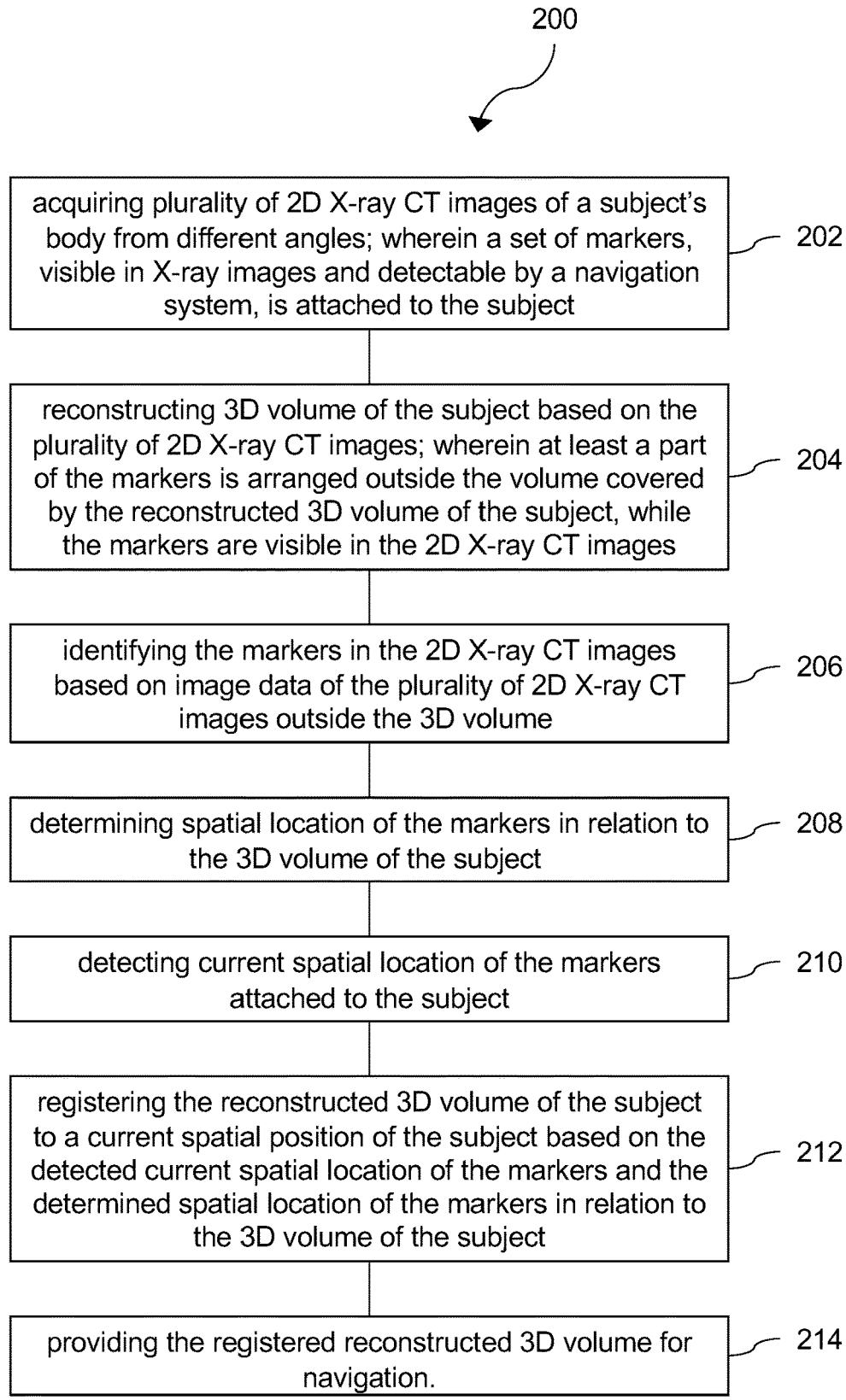
FIG. 3 shows steps of an example of a method for navigation support.

FIG. 3 shows steps of an example of a method 200 for navigation support. The method 200 comprises the following steps:

In an acquisition step 202, a plurality of 2D X-ray images of a subject's body are acquired from different angles. A set of markers, which are visible in X-ray images and which are detectable by a navigation system, is assigned to the subject.

In a reconstruction step 204, a 3D volume of the subject based on the plurality of 2D X-ray images is reconstructed. At least a part of the markers is arranged outside the volume covered by the reconstructed 3D volume of the subject, while the markers are visible in the 2D X-ray images.

In an identification step 206, the markers in the 2D X-ray images are identified based on image data of the plurality of 2D X-ray images outside the 3D volume, and in a determination step 208, a spatial location of the markers in relation to the 3D volume of the subject is determined.

In a detection step 210, a current spatial location of the markers assigned to the subject is detected.

In a registration step 212, the reconstructed 3D volume of the subject to a current spatial position of the subject is registered based on the detected current spatial location of the markers and the determined spatial location of the markers in relation to the 3D volume of the subject.

In a provision step 214, the registered reconstructed 3D volume is provided for navigation.

The method for navigation support can also be referred to as method for providing navigation support information.

As example, the plurality of 2D X-ray images is acquired by an X-ray imaging system. For example, the plurality of 2D X-ray images of a subject from different angles cover at least a range of 180°.

In another example, the plurality of 2D X-ray images of a subject from different angles cover at least a range of 110°, for example a range of about 110 to 150°.

For example, the markers are visible in some of the 2D X-ray images.

The current spatial location of the markers assigned to the subject is detected by a navigation system.

In an example of the method, for providing the registered reconstructed 3D volume for navigation, a spatial coordinate system of the plurality of 2D X-ray images is linked with a spatial coordinate system of a navigation system.

In an example, the markers are detected by a plurality of optical cameras attached to a mobile base structure. In an example, the markers are detected by an electromagnetic tracking arrangement attached to a mobile base structure.

In an example, all of the markers are arranged outside the 3D volume of the subject, while the markers are visible in some of the 2D X-ray images.

In an example, the 2D X-ray images relates to an imaged volume, wherein the reconstructed 3D volume forms a first sub-volume of the imaged volume and the rest of the imaged volume forms a second sub-volume. The first sub-volume and the second sub-volume form subsets of the imaged volume. The image data relating to the first sub-volume is used for the reconstruction of the 3D volume of the subject. The image data relating to the second sub-volume is used for the determining of the spatial location of the markers in relation to the 3D volume of the subject.

The 2D X-ray images comprise image data relating to spatial points, wherein a part of the spatial points is sufficiently covered by several images such that an accurate reconstruction is possible. The degree of coverage may be provided as a predetermined threshold.

Detecting a current spatial location of the markers can also be referred to as tracking the markers.

In an example, for the reconstructing, a first part of portions of the 2D X-ray images is selected, which allows a predetermined degree of accuracy of the reconstruction, while a second part of portions of the 2D X-ray images is de-selected.

In an example, the 2D X-ray images provide a 2D field of view of the subject, and the 3D volume of the subject provides a 3D field of view of the subject; wherein the 3D field of view is a selected part of the 2D field of view and the markers are arranged in the field of view outside the selected part of the 2D field of view.

Figure 3A:
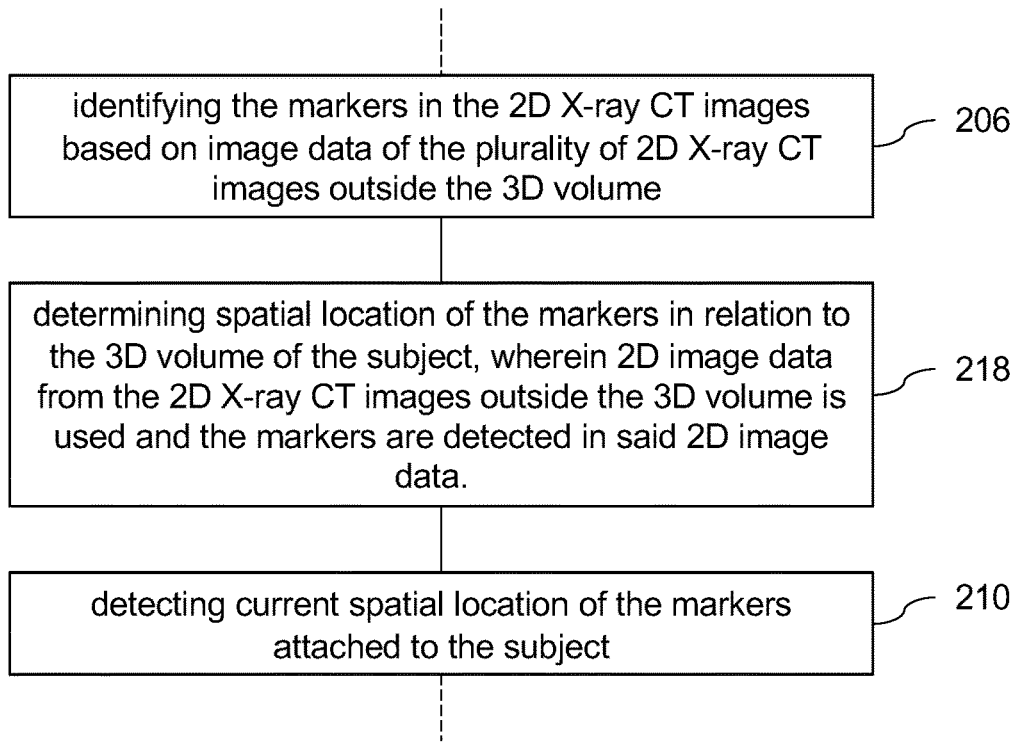
FIG. 3a shows a first variation for the determination step of FIG. 3.

FIG. 3a shows a first example of the determination step 208 described above in FIG. 3. According to FIG. 3a, for the determining of the spatial location of the markers in relation to the 3D volume of the subject, 2D image data from the 2D X-ray images outside the 3D volume is used 218 and the markers are detected in said 2D image data.

Figure 3B:
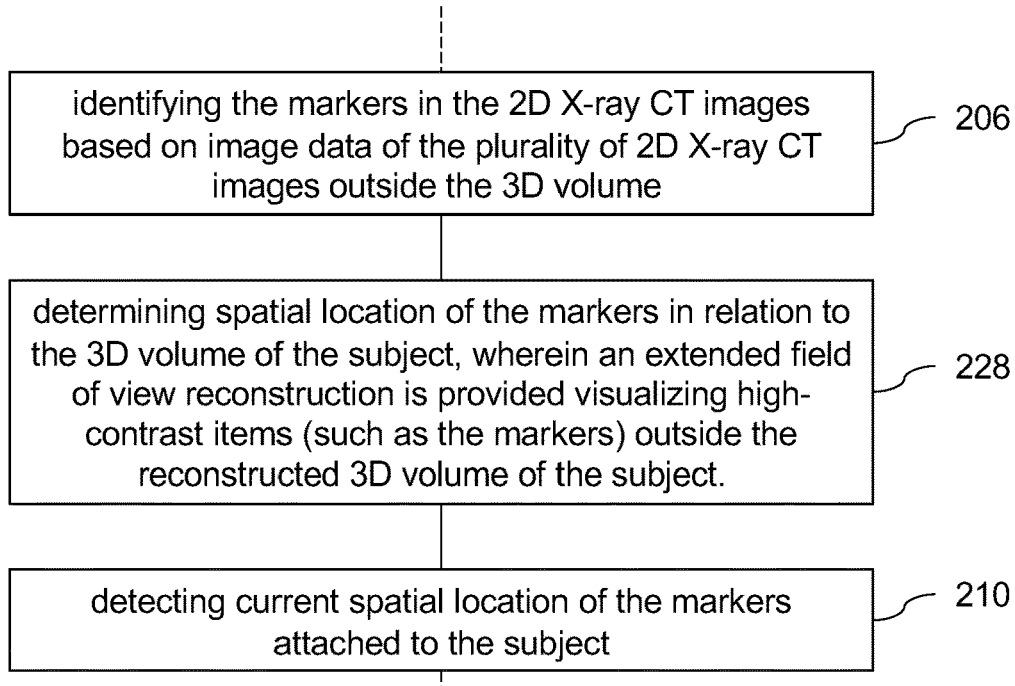
FIG. 3b shows a second variation for the determination step of FIG. 3.

FIG. 3b shows a second example of the determination step 208 described above in FIG. 3. According to FIG. 3b, provided alternatively or in addition to the previous example of FIG. 3a, for the determining of the spatial location of the markers in relation to the 3D volume of the subject, an extended field of view reconstruction is provided 228 visualizing high-contrast items (such as the markers) or items with a-priori knowledge regarding its shape or X-ray absorption properties outside the reconstructed 3D volume of the subject.

In an example of the method, for the detection, information about the shape of the markers is provided.

In an example, voxels outside the 3D volume of the subject are subject to filtering by applying a threshold and to change all voxels below a predetermined threshold to a predetermined image value, e.g. change the voxel to black. In another example, voxels belonging to the 3D volume of the subject are indicated, e.g. with a circle enclosing the 3D volume of the subject.

Figure 4:
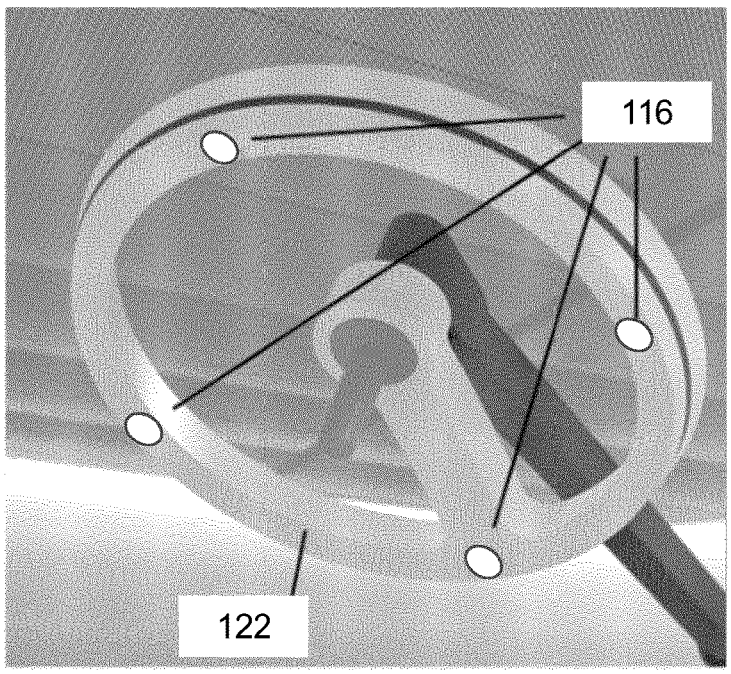
FIG. 4 shows an example of optical cameras attached to a mobile base structure.

FIG. 4 shows an example of a plurality of the optical cameras 116 attached to the ring-like support 122. The cameras 116 are configured to detect the markers.

In another option, a single optical camera is provided that is configured to detect the markers.

In FIG. 5, an example is shown, according to which a set of markers 136 is provided, which markers 136 are configured for temporal assignment to the subject 128. As indicated, the set of markers is temporarily assigned to a subject, for example prepared around or outside an area of a planned intervention. In an example, the markers 136 are configured to be assigned to the subject outside a region of interest, which region of interest is set to be covered by the reconstructed 3D volume.

Also shown is a display 138 that may be provided as graphical user interface of a not further shown control console. The display 138 can be provided as a tablet display.

FIG. 5a shows another example of the markers 136 of FIG. 5. It is noted that the markers 136 are shown in a non-symmetrical pattern. In a preferred example, the markers 136 are provided in an irregular pattern.

In another example, the markers 136 are provided in a regular pattern.

In a further example, the markers 136 are provided in a symmetrical pattern.

The markers 136 may be provided to be detectable in relation to their spatial rotational angle. In an example, the markers 136 are provided to be detectable in a 2D X-ray image with their respective six degrees of freedom of movement, i.e. their possible location and orientation in space.

In an example, the markers 136 are provided as individual markers arranged to provide a marker field, such as in FIG. 5a. The markers 136 may be provided as individual physical objects. In an option, the markers 136 are provided as individual markers. In another option, the markers 136 are provided as a set of markers.

Figure 5B:
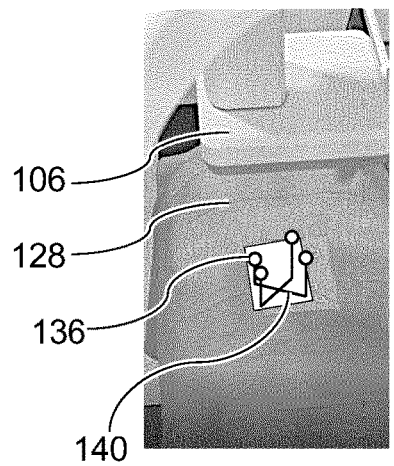
FIG. 5b shows a further example of markers.

In another example, the markers 136 are provided as connected markers arranged to provide a marker array, such as in FIG. 5b. The markers 136 may be provided attached to a marker base 140 to form a single physical object. The marker base 140 can be attached to the subject.

Figure 6A:
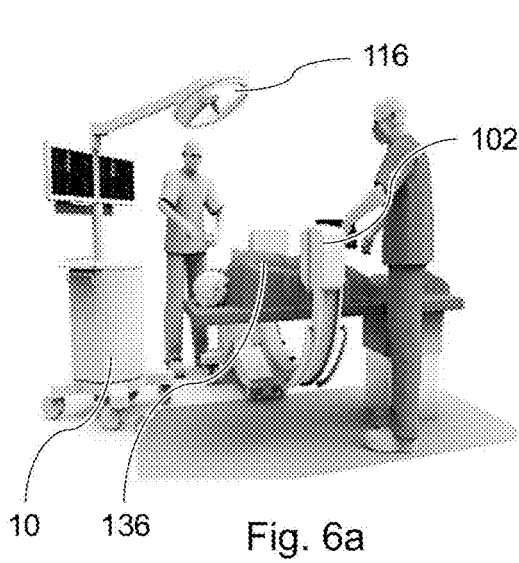
FIG. 6a shows a first and FIG. 6b shows a second exemplary imaging position of the navigated X-ray imaging arrangement.
Figure 6B:
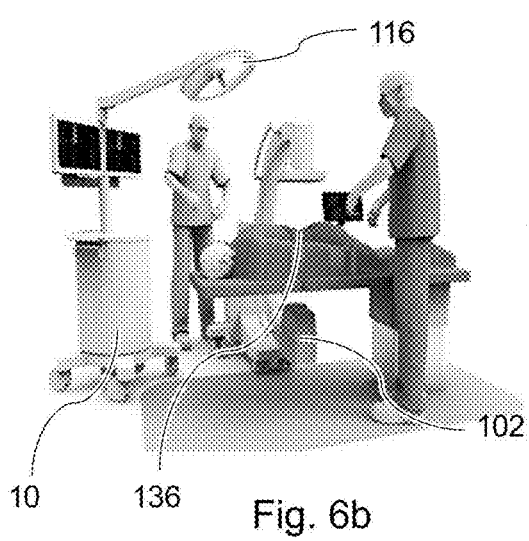

FIG. 6a and FIG. 6b show an example where the navigation system is attached to a so-called mobile view station, which is physically separated from the X-ray imaging system 102.

FIG. 6a shows the navigated X-ray imaging arrangement 100 in a first imaging position. As can be seen, the X-ray source 104 and the X-ray detector 106 are arranged to provide an imaging direction from the side of the subject, e.g. approximately horizontal.

FIG. 6b shows the navigated X-ray imaging arrangement 100 in a second imaging position. As can be seen, the X-ray source 104 and the X-ray detector 106 are arranged to provide an imaging direction from below the subject, e.g. approximately vertical.

The X-ray visible markers 136 are detected, e.g. automatically, in a subset of the 2D X-ray images, e.g. the first position and the second position) and the detected markers 136 are used to calculate the 3D position of the markers within the extended 3D cone beam CT volume.

Figure 7A:
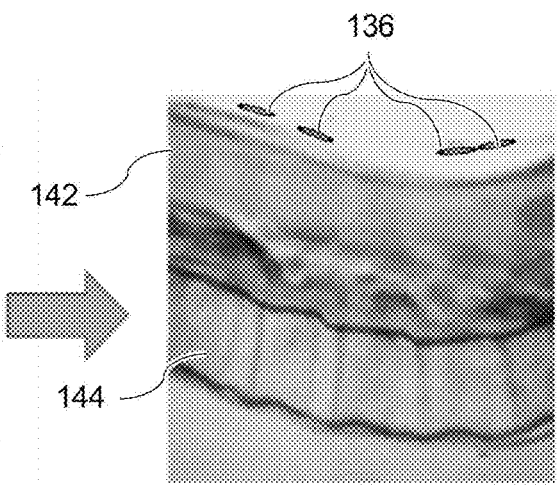
FIG. 7a shows a first and FIG. 7b shows a second resulting acquired X-ray image.

FIG. 7a shows a first X-ray image 142 of a spine structure 144 as a result of an X-ray acquisition of the navigated X-ray imaging arrangement 100 in the first imaging position. The markers 136 are visible in the upper portion of the first X-ray image 142.

Figure 7B:
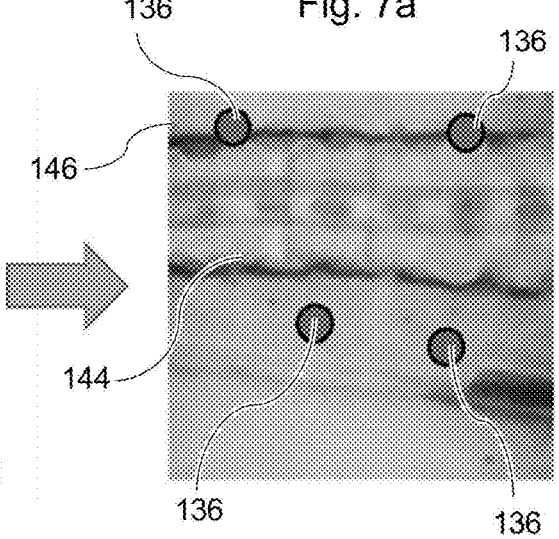

FIG. 7b shows a second X-ray image 146 of the spine structure 144 as a result of an X-ray acquisition of the navigated X-ray imaging arrangement 100 in the second imaging position. The markers 136 are visible in the upper portion and middle portion of the second X-ray image 146.

Figure 8:
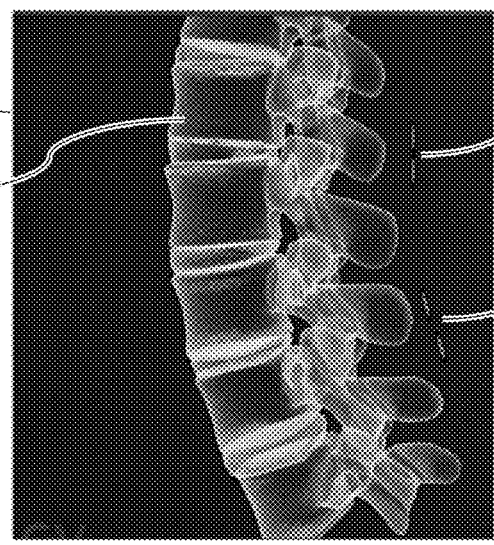
FIG. 8 shows an example of a registered reconstructed 3D volume for navigation.

FIG. 8 shows an illustration 148 of an example of a registered reconstructed 3D volume for navigation. FIG. 8 shows a side view of the spine structure 144. The spine structure 144 is visible and the markers 136 are also depicted.

FIG. 6a and FIG. 6b show that X-ray visible markers are detected in a subset of the 2D X-ray images of FIG. 7a and FIG. 7b, e.g. in the first position and the second position, and used to calculate the 3D position of the markers within the extended 3D cone beam CT volume as shown in FIG. 8.

Figure 9A:
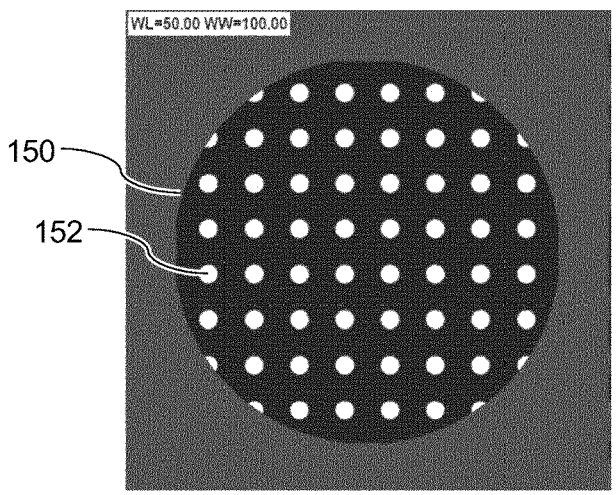
FIG. 9 shows an example for different field of view reconstructions.
Figure 9B:
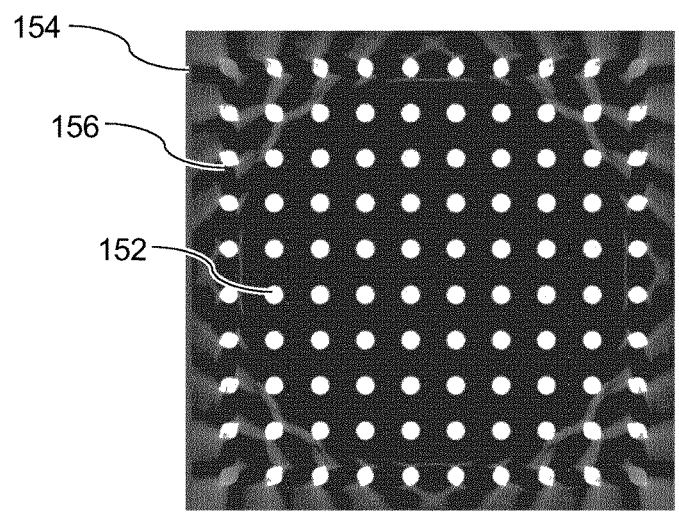
Figure 9C:
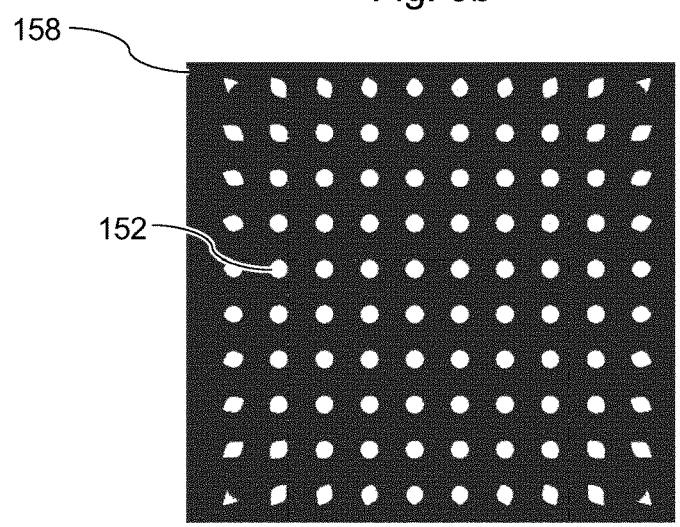

FIG. 9a, FIG. 9b and FIG. 9c show examples for different field of view reconstructions for further explanation.

FIG. 9a shows a standard field of view reconstruction 150. Markers are shown as a number of highlighted dots 152. As can be seen, only markers within a circular center field are sufficiently covered by the 2D CT scans to be able to identify them and to show them in the image.

FIG. 9b shows an extended field of view reconstruction 154. Markers outside the center field are indicated, but not as precise as the markers within the standard field of view, e.g. indicated with reference numeral 156.

FIG. 9c shows a threshold extended field of view reconstruction 158. Most markers outside the center field are indicated with their correct center of gravity.

In a further example, not shown, a correct reconstruction after correction is provided showing a uniform grid of circular dots.

The arrangement of the markers 136 larger than the 3D field of view, itself moving the markers out of the reconstruction space, is compensated for, i.e. solved by one of the imaging processes described above.

The relation of the 2D images and the 3D volume is known from the CT imaging process. The 3D field of view may be provided as a 3D cylinder. The 3D field of view is based on voxels seen by a sufficient number of 2D images, thus allowing the reconstruction of the 3D volume. In an example, the 3D volume relates to points in space seen in all projections.

In an option, 2D images are provided and if the markers are distance enough, and the 3D geometry of the markers pattern is known, the markers are detectable in 2D even with a depth estimation. The 3D volume is thus kept free of marker parts. The location of markers outside the area for accurate reconstruction thus improves the accuracy of the reconstruction.

In an example, reconstruction accuracy is provided when a location or center point of a marker needs to deviate less than 1 mm from the actual physical location to be detectable.

The parts insufficiently covered by the 2D images is used for marker detection and location.

Briefly said, the difference (or delta) of the 2D field of view and the 3D field of view is used for registration of the markers.

The markers outside the 3D field of view thus belong to image data which for itself is less reliable, but just good enough for the marker location detection and determination respectively.

The image parts of the markers outside the 3D field of view may be subject to deformation, but when geometric information is used, such as known size and shape of the markers, the image data can be adapted, i.e. corrected accordingly. As an example, in 2D images, the center point is detected in 3D and models of the markers are used for more detailed location detection.

Thus, knowledge is added in 3D to modify the 3D data. In an example, the determined location of the markers is communication by adding the information to the 3D volume or to send them as separate meta data attached to the 3D data.

The term "subject" may also be referred to as individual. The "subject" may further also be referred to as patient, although it is noted that this term does not indicate whether any illness or disease is actually present with the subject.

As an effect, in an example, an optical navigation system performs automatic registration with a small field of view X-ray system that is compatible with generic small field of view C-arm systems, but without optical markers on the X-ray system.

A field of application are 3D capable mobile C-arm X-ray systems, e.g. 3D mobile C-arm project interventional guided therapy systems. A further field of application are optical navigation systems.

In an example, a computer program is provided comprising computer readable code or instructions which when executed by a processor enable the processor to carry out the method of one of the examples above.

In another example, a computer program or program element for controlling an apparatus according to one of the examples above is provided, which program or program element, when being executed by a processing unit, is adapted to perform the method steps of one of the method examples above.

In a further example, a computer readable medium having stored the computer program of the preceding example is provided.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit or be distributed over more than one computer units, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

Aspects of the invention may be implemented in a computer program product, which may be a collection of computer program instructions stored on a computer readable storage device which may be executed by a computer. The instructions of the present invention may be in any interpretable or executable code mechanism, including but not limited to scripts, interpretable programs, dynamic link libraries (DLLs) or Java classes. The instructions can be provided as complete executable programs, partial executable programs, as modifications to existing programs (e.g. updates) or extensions for existing programs (e.g. plugins). Moreover, parts of the processing of the present invention may be distributed over multiple computers or processors.

As discussed above, the processing unit, for instance a controller implements the control method. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system for navigation support, the system comprising:
   a marker detecting arrangement configured to detect a current spatial location of a set of markers assigned to a subject;
   a processor is configured to:
   receive a plurality of 2D X-ray images of the subject from different angles, wherein the set of markers are visible in the X-ray images;
   reconstruct a 3D volume of the subject based on the plurality of 2D X-ray images; wherein at least a part of the set of markers is positioned outside volume covered by the reconstructed 3D volume of the subject;
   identify at least the part of the set of markers in the plurality of 2D X-ray images based on image data of the plurality of 2D X-ray images outside the 3D volume and determine a spatial location of the set of markers in relation to the 3D volume of the subject;
   register the reconstructed 3D volume of the subject to a current spatial position of the subject based on the current spatial location of the set of markers as detected by the marker detecting arrangement and the determined spatial location of the set of markers in relation to the 3D volume of the subject; and
   provide the registered reconstructed 3D volume for navigation support.

2. The system according to claim 1, wherein for the determination of the spatial location of the set of markers in relation to the 3D volume of the subject, the processor is further configured to use 2D image data from the plurality of 2D X-ray images outside the 3D volume of the subject and to detect the set markers in the 2D image data.

3. The system according to claim 1, wherein for the determining of the spatial location of the set of markers in relation to the 3D volume of the subject, the processor is further configured to provide an extended field of view reconstruction including a visualization of high-contrast items or items for which a-priori knowledge is available regarding a shape or X-ray absorption properties, the items appearing in the 2D image data outside the 3D volume of the subject.

4. The system according to claim 1, wherein the marker detecting arrangement comprises a plurality of optical cameras configured to detect the markers.

5. The system according to claim 1, wherein the marker detecting arrangement comprises an electromagnetic tracking arrangement attached to a base, the electromagnetic tracking arrangement configured to detect the set of markers.

6. The system according to claim 1, wherein for the detection of the set of markers in the 2D image data from the plurality of 2D X-ray images outside the 3D volume of the subject, the processor is further configured to provide information about at least one of a shape of the set of markers and X-ray absorption properties of the set of markers and use the information for artifact correction before detection of the markers.

7. The system according to claim 1, further comprising:
an X-ray imaging system configured to acquire 2D X-ray images from a plurality of angles for providing the plurality of acquired 2D X-ray images of the subject; and
wherein the processor is further configured to link a spatial coordinate system of the X-ray imaging system with a spatial coordinate system of the marker detecting arrangement.

8. The system according to claim 7, further comprising a plurality of at least two markers configured for temporal assignment to the subject.

9. The system according to claim 7, wherein the markers are configured to be assigned to the subject, which may be outside a region of interest, which region of interest is set to be covered by the reconstructed 3D volume.

10. A method for navigation support, the method comprising the following steps:
acquiring a plurality of 2D X-ray images of a subject's body from different angles; wherein a set of markers, which are visible in X-ray images and which are detectable by a navigation system, is assigned to the subject;
reconstructing a 3D volume of the subject based on the plurality of 2D X-ray images; wherein at least a part of the set of markers is arranged outside the volume covered by the reconstructed 3D volume of the subject, while the markers are visible in the plurality of 2D X-ray images;
identifying the set of markers in the 2D X-ray images based on image data of the plurality of 2D X-ray images outside the 3D volume, and determining a spatial location of the set of markers in relation to the 3D volume of the subject;
detecting a current spatial location of the set of markers assigned to the subject;
registering the reconstructed 3D volume of the subject to a current spatial position of the subject based on the detected current spatial location of the set of markers and the determined spatial location of the set of markers in relation to the 3D volume of the subject; and
providing the registered reconstructed 3D volume for navigation support.

11. The method according to claim 10, wherein for the determining of the spatial location of the markers in relation to the 3D volume of the subject, 2D image data from the plurality of 2D X-ray images outside the 3D volume is used and the set of markers are detected in said 2D image data.

12. The method according to claim 10, wherein for the determining of the spatial location of the markers in relation to the 3D volume of the subject, an extended field of view reconstruction is provided including a visualization of high-contrast items or items for which a-priori knowledge is available regarding a shape or X-ray absorption properties, the items appearing in the 2D image data outside the 3D volume of the subject.

13. A non-transitory computer-readable storage medium having stored a computer program comprising instructions which, when executed by a processor, cause the processor to:
acquire a plurality of 2D X-ray images of a subject's body from different angles, wherein a set of markers, which are visible in X-ray images and which are detectable by a navigation system, is assigned to the subject;
reconstruct a 3D volume of the subject based on the plurality of 2D X-ray images, wherein at least a part of the set of markers is arranged outside the volume covered by the reconstructed 3D volume of the subject, while the markers are visible in the plurality of 2D X-ray images;
identify the set of markers in the 2D X-ray images based on image data of the plurality of 2D X-ray images outside the 3D volume, and determining a spatial location of the set of markers in relation to the 3D volume of the subject;
detect a current spatial location of the set of markers assigned to the subject;
register the reconstructed 3D volume of the subject to a current spatial position of the subject based on the detected current spatial location of the set of markers and the determined spatial location of the set of markers in relation to the 3D volume of the subject; and
provide the registered reconstructed 3D volume for navigation support.

* * * * *